US006361496B1

(12) United States Patent
Zikorus et al.

(10) Patent No.: US 6,361,496 B1
(45) Date of Patent: *Mar. 26, 2002

(54) PRESSURE TOURNIQUET WITH ULTRASOUND WINDOW AND METHOD OF USE

(75) Inventors: Arthur W. Zikorus, San Jose; John D'Angelo, Morgan Hill; Brian E. Farley, Los Altos, all of CA (US)

(73) Assignee: VNUS Medical Technologies, Inc., San Jose, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/322,326

(22) Filed: May 28, 1999

Related U.S. Application Data

(62) Division of application No. 08/867,131, filed on Jun. 2, 1997, now Pat. No. 6,231,507.

(51) Int. Cl.[7] ................................................ A61B 8/00
(52) U.S. Cl. ...................... 600/437; 600/443; 606/203
(58) Field of Search ................................. 600/438, 459, 600/485–480, 483, 489, 490, 495, 588, 453–455; 606/202–203

(56) References Cited

U.S. PATENT DOCUMENTS

| 373,339 A | 11/1887 | Hamilton |
| 659,409 A | 10/1900 | Mosher |
| 833,759 A | 10/1906 | Sourwine |
| 985,865 A | 3/1911 | Turner, Jr. |
| 3,230,957 A | 1/1966 | Seifert |

(List continued on next page.)

FOREIGN PATENT DOCUMENTS

| DE | 19 00863 | 1/1969 |
| DE | 35 16830 A1 | 11/1986 |

(List continued on next page.)

OTHER PUBLICATIONS

Watts, Endovenous Diathermy Destruction of Internal Saphenous, British Medical Journal, Oct. 7, 1972, p. 53.
O'Reilly, Endovenous Diathermy Sclerosis as a Unit of the Armamentarium for the Attack on Varicose Veins, The Medical Journal of Australia, Jun. 1, 1974, p. 900.

(List continued on next page.)

Primary Examiner—Francis J. Jaworski
(74) Attorney, Agent, or Firm—Fulwider Patton Lee & Utecht, LLP (57) ABSTRACT

A pressure tourniquet having a window transparent to ultrasound is wrapped around a leg or another anatomical structure containing veins. An ultrasound transducer is placed in contact with the window of the tourniquet. The window is adjacent the anatomical structure and the transducer probes a dilated vein with ultrasound. The transducer can measure the size of the vein and detect reflux. A pneumatic bladder on the tourniquet is inflated to apply pressure to the anatomical structure so that the vein is compressed by the tissue of the surrounding anatomical structure. As pressure from the tourniquet reduces the diameter of the vein, competency of the vein valve can be temporarily restored to indicate the proper reduced diameter required to restore venous function. An electrode catheter is introduced into the vein to apply energy for durably molding the vein to the reduced diameter.

37 Claims, 6 Drawing Sheets

U.S. PATENT DOCUMENTS

| | | | |
|---|---|---|---|
| 3,301,258 A | | 1/1967 | Werner et al. |
| 3,527,197 A | * | 9/1970 | Wave .......................... 600/453 |
| 3,552,382 A | * | 1/1971 | Mount ......................... 600/453 |
| 3,557,794 A | | 1/1971 | Van Pattern |
| 3,920,021 A | | 11/1975 | Hiltebrandt |
| 4,016,886 A | | 4/1977 | Doss et al. |
| 4,043,338 A | | 8/1977 | Homm et al. |
| 4,119,102 A | | 10/1978 | Le Veen |
| 4,127,114 A | * | 11/1978 | Bretscher ................... 600/480 |
| 4,154,246 A | | 5/1979 | LeVeen |
| 4,312,364 A | | 1/1982 | Convert et al. |
| 4,346,715 A | | 8/1982 | Gammell |
| 4,494,550 A | | 1/1985 | Blazek et al. |
| 4,522,205 A | | 6/1985 | Taylor et al. |
| 4,643,186 A | | 2/1987 | Rosen et al. |
| 4,660,571 A | | 4/1987 | Hess et al. |
| 4,664,120 A | | 5/1987 | Hess |
| 4,699,147 A | | 10/1987 | Chilson et al. |
| 4,776,349 A | | 10/1988 | Nashef et al. |
| 4,807,620 A | | 2/1989 | Strul et al. |
| 4,823,812 A | | 4/1989 | Eshel et al. |
| 4,841,980 A | | 6/1989 | Lee et al. |
| 4,926,874 A | * | 5/1990 | Lee ........................... 600/495 |
| 4,945,912 A | | 8/1990 | Langberg |
| 4,966,597 A | | 10/1990 | Cosman |
| 4,976,711 A | | 12/1990 | Parins et al. |
| 4,979,948 A | | 12/1990 | Geddes et al. |
| 5,010,894 A | | 4/1991 | Edhag |
| 5,057,107 A | | 10/1991 | Parins et al. |
| 5,078,717 A | | 1/1992 | Parins et al. |
| 5,117,828 A | | 6/1992 | Metzger et al. |
| 5,122,137 A | | 6/1992 | Lennox |
| 5,156,151 A | | 10/1992 | Imran |
| 5,188,602 A | | 2/1993 | Nichols |
| 5,193,549 A | * | 3/1993 | Bellin et al. ................ 600/480 |
| 5,215,103 A | | 6/1993 | Desai |
| 5,255,678 A | | 10/1993 | Deslauriers, et al. |
| 5,263,493 A | | 11/1993 | Avitall |
| 5,293,869 A | | 3/1994 | Edwards et al. |
| 5,383,917 A | | 1/1995 | Desai et al. |
| 5,397,339 A | | 3/1995 | Desai |
| 5,405,322 A | | 4/1995 | Lennox et al. |
| 5,409,000 A | | 4/1995 | Imran |
| 5,409,010 A | | 4/1995 | Beach |
| 5,411,025 A | | 5/1995 | Webster, Jr. |
| 5,413,582 A | | 5/1995 | Eaton |
| 5,423,815 A | | 6/1995 | Fugo |
| 5,437,664 A | | 8/1995 | Cohen et al. |
| 5,449,381 A | | 9/1995 | Imran |
| 5,458,596 A | | 10/1995 | Lax et al. |
| 5,465,717 A | | 11/1995 | Imran et al. |
| 5,505,730 A | | 4/1996 | Edwards |
| 5,514,130 A | | 5/1996 | Baker |
| 5,545,161 A | | 8/1996 | Imram |
| 5,556,396 A | | 9/1996 | Cohen et al. |
| 5,709,224 A | | 1/1998 | Behl et al. |

FOREIGN PATENT DOCUMENTS

| | | |
|---|---|---|
| EP | 0 189 329 A2 | 7/1986 |
| WO | WO 95/10322 | 4/1920 |
| WO | WO 92/12681 | 8/1992 |
| WO | WO 94/07446 | 4/1994 |
| WO | WO 96/28088 | 9/1996 |
| WO | WO 97/18679 | 5/1997 |

OTHER PUBLICATIONS

O'Reilly, Ednovenous Diathermy Sclerosis fo Varicose Veins, The Australia, New Zealand Journal of Surgery, vol. 47, No. 3, Jun. 1977, pp. 393–395.

O'Reilly, A Technique of Diathermy Sclerosis of Varicose Veins, The Australia, New Zealand Journal of Surgery, vol. 51, No. 4, Aug. 1981, pp. 379–382.

Cragg et al., Endovascular Diathermic Vessel Occlusion, Diagnostic Radiology, 144: 303–308, Jul. 1982.

van Bemmelen, Quantitative Segmental Evaluation of Venous Valvular Reflux with Duplex Ultrasound Scanning, J. Vasc. Surg. 1989. 10:425–431.

Partsch, Compression Therapy of the Legs, J. Dermatol. Surg. 1991; 17:79–805.

Sarin et al., Mechansim of Action of External Compression on Venous Function, J. Surg., vol. 79, No. 6, Jun. 1992.

Money, endovascular Electroblation of Peripheral Veins, 22nd Annual Symposium, Current Critical Problems, New Horizons and Techniques in Vascular and Endovascular Surgery (Nov. 1995).

Crockett, et al., Preliminary Experience With An Endovascular Catheter For Electrocoagulation of Peripheral Veins, The Journal of Vascular Technology, Winter 1996, at 19–22.

* cited by examiner

PRESSURE TOURNIQUET WITH ULTRASOUND WINDOW AND METHOD OF USE

This application is a divisional of Ser. No. 08/867,131 filed Jun. 2, 1997 and now U.S. Pat. No. 6,231,507.

BACKGROUND OF THE INVENTION

The invention relates to a non-invasive compressive device for use with ultrasound, and more particularly to a pressure tourniquet having a window that is transparent to ultrasound and a method of use.

The venous system contains a plurality of valves for directing blood flow to the heart. The venous system of the lower limb consists essentially of the superficial venous system and the deep venous system with perforating veins connecting the two systems. The superficial system includes the great saphenous vein and the small saphenous vein. The deep venous system includes the anterior and posterior tibial veins which unite to form the popliteal vein which in turn becomes the femoral vein when joined by the small saphenous vein.

Venous valves are usually bicuspid valves, with each cusp forming a sack or reservoir for blood which, under pressure, forces the free edges of the cusps together to prevent retrograde flow of the blood and allow only antegrade flow to the deep veins and heart. When an incompetent valve attempts to close in response to a pressure gradient across the valve, the cusps do not seal properly and retrograde flow of blood occurs. Venous insufficiency is a chronic disease involving the incompetence of venous valves.

Chronic venous insufficiency is a problem caused by hydrodynamic forces acting on the lowest part of the body, the legs, ankles and feet. As the veins dilate due to increased pressure, the valves in the veins become less able to withstand the weight of the blood above them. The weight of the blood causes the veins to dilate further and the valves in the veins to fail. Localized incompetence of a venous valve allows reflux of blood from the deep venous system to the superficial venous system. Reflux may be expressed as the peak reverse velocity of blood as a function of vein diameter. Patients with phlebitis may have damaged vein valve leaflets. A non-invasive manner of assessing the structural integrity or competency of venous valves is needed.

Patients who develop chronic venous insufficiency of the lower extremities frequently develop complications of this disease, including skin discoloration, varicose veins, and ulcerations. These patients may develop blood clots in their legs which can travel to their lungs, resulting in a pulmonary embolism. These complications develop over time, with increasingly severe damage to the veins and the valves within the veins.

The morphology of venous disease can be determined by the descending venography. This study requires that patients have an intravenous catheter placed in their groin and have multiple injections of radiographic contrast material injected while having multiple x-rays taken of the legs. The patient is held in various positions and tilted to allow the contrast material to flow into the veins. However, the contrast material has inherent medical risks of allergic or anaphylactic reactions. In addition, needles and canulas are placed into the patient at multiple sites for contrast injection.

Continuous-wave (CW) doppler is a commonly used method of evaluating venous reflux. This method, however, cannot determine precisely which veins in the path of the sound beam are being detected, thereby creating uncertainty about the vein being examined at the treatment site. Duplex ultrasound scanning can allow precise localization of the area being tested, as well as detect changes in flow direction. Both imaging, for localizing a vein, and Doppler processing, to detect flow and flow direction, are provided. When evaluating venous valve incompetence, the valves under evaluation should be closed. To elicit reflux for Doppler or ultrasound evaluation, the methods of the Valsalva maneuver, and compression of the limb containing the veins can be used with the patient in the supine and upright positions. Standardized compression can be achieved with pneumatic cuffs.

The Valsalva maneuver can be used by the patient to increase abdominal pressure to induce reflux in the lower limb. The Valsalva maneuver involves a forced expiratory effort against an airway, the strain of this effort causing high intrathoracic pressure which impedes venous return. However, the Valsalva maneuver has a variable effect on femoral venous diameter and on distal deep venous pressure when the patient is in the supine position. The reflux produced can be of variable duration because of the variable anatomic presence of the ileofemoral valves. When an ultrasound transducer is distal to a functioning valve at this level, the Valsalva maneuver does not produce the necessary transvalvular pressure gradients for closure of the valve.

Reflux in veins can be decreased by external compression. Pneumatic compression devices have been used to obtain closure of a venous valve with physiologic transvalvular pressure gradients. A cuff placed around a leg is inflated and rapidly deflated to simulate muscle relaxation to elicit valve closure. The cuff is located distal to the ultrasound transducer. The distance between the release of distal compression and the transducer is small to facilitate locating the site of venous incompetence. The area of the limb which is compressed by the cuff cannot be evaluated by ultrasound, so such measurements are taken along areas adjacent the tourniquet. A water-filled cuff has been proposed to vary the applied pressure to a limb while allowing ultrasound imaging of the veins through the cuff. However, disadvantages to this approach exist. The water-filled cuff can be bulky, heavy, and may not present a uniform or consistent ultrasound medium. If the cuff is constructed of an inelastic material, the cuff may contain air bubbles or form an irregular contact surface for the ultrasound transducer depending on the amount of water filling the cuff. Water leaks can arise that interfere with the operation of the cuff.

After determining the sites of venous incompetence, treatments such as compressive stockings worn about the patient's limb are often used to treat the disorder. However, it may be required to use such compressive stockings on a daily basis which could result in major lifestyle changes for the patient. Indirect valvuloplasty is another procedure in which an inelastic polyester cuff is wrapped around the vein itself to reduce the diameter of the vein. However, such a surgical procedure can be laborious and highly invasive, which has its associated complications with risk to life and expense.

Hence, there is a need for a system and method that would allow for a non-invasive or minimally invasive assessment of the condition of the veins and to locate incompetent valves. There also exists a need for a system that can determine the amount of diameter reduction of the vein in order to improve coaptation of venous valves and venous function. Such a system and method should be capable of being used in conjunction with a treatment that would durably reduce the diameter of a dilated vein to restore venous function. The invention fulfills these needs and others.

SUMMARY OF THE INVENTION

Briefly, and in general terms, the present invention provides an apparatus and method for testing veins, identifying incompetent venous valves, and treating venous disorders. The apparatus includes a compression device adapted to apply external pressure to a patient to compress a selected vein to a reduced diameter, and a window substantially transparent to ultrasound and located on the compression device so as to allow the reduced diameter portion of the vein to be viewed by ultrasound. The compression device can include an inflatable bladder.

The method in accordance with the present invention detects reflux and measures the diameter of the vein. The method includes the steps of placing a tourniquet around an anatomical structure containing the vein, the tourniquet having a window transparent to ultrasound, applying pressure to the anatomical structure with the tourniquet until a selected reduced diameter for the vein is achieved, whereby the vein diameter is affected by the pressure applied by the tourniquet, and monitoring the vein diameter by ultrasound through the window. Blood velocity in the vein can also be monitored by ultrasound. Energy can be applied to the vein from an electrode catheter to shrink the vein so that the vein remains at the reduced diameter produced by the external compressive force of the tourniquet.

One aspect of the present invention is that a tourniquet for applying pressure to an anatomical structure such as a limb includes a window transparent to ultrasound.

Another aspect of the present invention is that the window on the tourniquet allows an ultrasound transducer to detect reflux in a dilated vein in the limb covered by the window, and to determine the diameter of the vein for diagnosis and treatment.

A further aspect of the present invention is that the tourniquet applies pressure to the vein in order to reduce the diameter of the vein and restore venous function.

Yet another aspect of the present invention is that an electrode catheter can be introduced into the vein to apply energy to heat and mold the vein so that the vein will remain at the reduced diameter set by the pressure tourniquet.

Another aspect of the present invention is to temporarily set a reduced diameter for the vein so that a catheter prevents the vein from shrinking beyond the reduced diameter during treatment when energy is applied from either inside the vein or outside the vein.

Yet another aspect of the present invention is that a second tourniquet is used distal to the first tourniquet to occlude the vein and prevent blood flow in order to provide a more consistent and predictable shrinking of the vein by the electrode catheter by diminishing the effect-of blood flow through the vein.

Yet a further aspect of the present invention is that a balloon on the catheter can be used to occlude and prevent blood flow during treatment in order to provide a more consistent and predictable heating of the vein.

These and other aspects and advantages of the present invention will become apparent from the following detailed description in conjunction with the accompanying drawings.

DETAILED DESCRIPTION OF THE EMBODIMENTS

Figure 1:
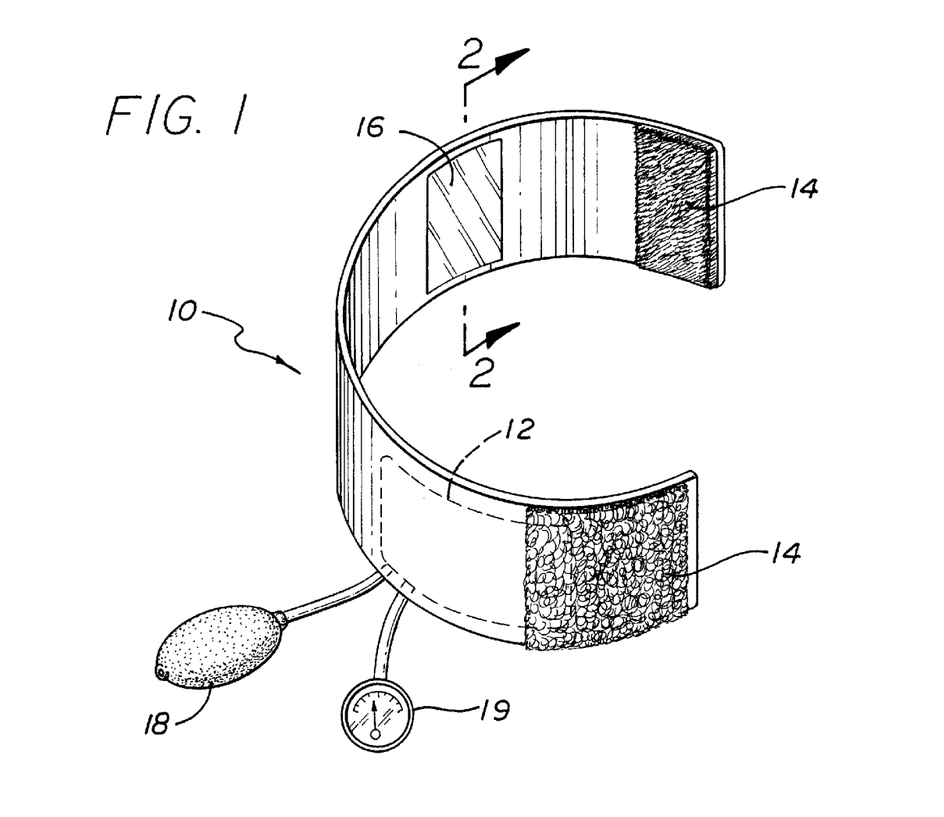
FIG. 1 is a perspective view of a pressure tourniquet having a window in accordance with the present invention.

Referring to the drawings, and in particular to FIG. 1, there is shown a pressure tourniquet 10 having an inflatable bladder 12, a fastener 14, and a window 16 substantially transparent to acoustic energy, in particular ultrasonic energy or ultrasound. The tourniquet preferably accommodates a range of diameters for a patient's limb, such as between twenty and forty centimeters. The bladder 12 preferably occupies only a portion of the tourniquet. A hand pump 18 can be attached to the bladder 12 in order to provide air to inflate the bladder. The use of air instead of another fluid such as water lessens the weight of the tourniquet. A pressure monitoring gauge 19 monitors the inflation pressure of the bladder. The pressure gauge 19 can be used as a relative reference of inflation pressure in conjunction with changes in reflux patterns as measured by duplex ultrasound. The fastener 14 can be a hook and loop system so that an adaptable fit can be achieved for different patients.

Figure 2A:
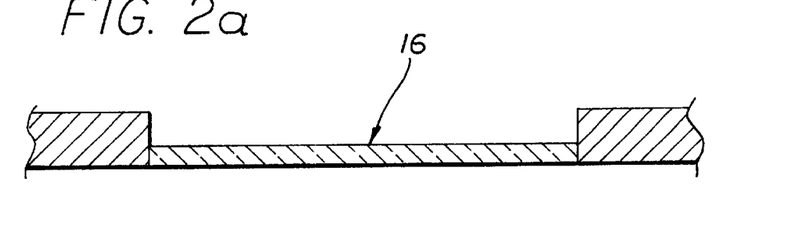
FIG. 2a is a cross-sectional view along lines 2—2 of FIG. 1 of one embodiment of the tourniquet in accordance with an aspect of the present invention.

As illustrated in FIG. 2a, the window 16 is preferably a vertically biased echo-lucent window to allow ultrasound imaging with a standard ultrasound transducer. The window 16 can be fabricated from a thin flexible polymer, nylon, polyurethane film, or other material transparent to ultrasound. Such materials preferably minimize any echoing of ultrasound energy. Nylon is often dyed, which renders the material opaque. A thin polyurethane film substantially transparent to light can be used in order to allow external visualization of the limb. For example, markings on the limb may be used to ensure proper placement of the window and the tourniquet over the desired diagnosis or treatment site. The polyurethane film can have any thickness. Polyurethane film between about 0.003 to 0.015 inches (about 0.07 millimeters to 0.35 millimeters) would have a suitable thickness for a visually transparent echo-lucent window.

Figure 2B:
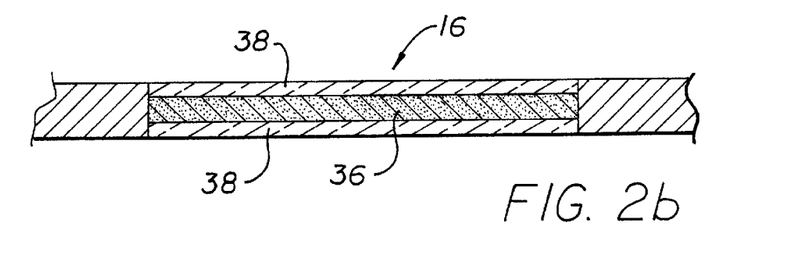
FIG. 2b is a cross-sectional view along lines 2—2 of FIG. 1 of another embodiment of the tourniquet in accordance with the present invention.

In another embodiment, as illustrated in FIG. 2b, the window is a gel pouch that comprises an ultrasound medium in the form of a gel 36 contained between two layers of polyurethane 38 connected together in order to form the pouch. The gel pouch can be translucent through the gel and layers of polyurethane. Flexible polymers other than polyurethane can be used to form the pouch. The gel pouch has a thickness to function as a stand-off for the ultrasound transducer from the patient's limb. Acting as a stand-off, the gel pouch provides the focal length required for the ultrasound to assess veins near the surface of the limb. A gel pouch located adjacent or within the inflation bladder can approximate the increased thickness of the bladder when inflated so as to facilitate engagement by the ultrasound transducer. The thickness of the gel pouch window prevents the inflating bladder from pulling the ultrasound window away from the skin so that contact is maintained.

Figure 3:
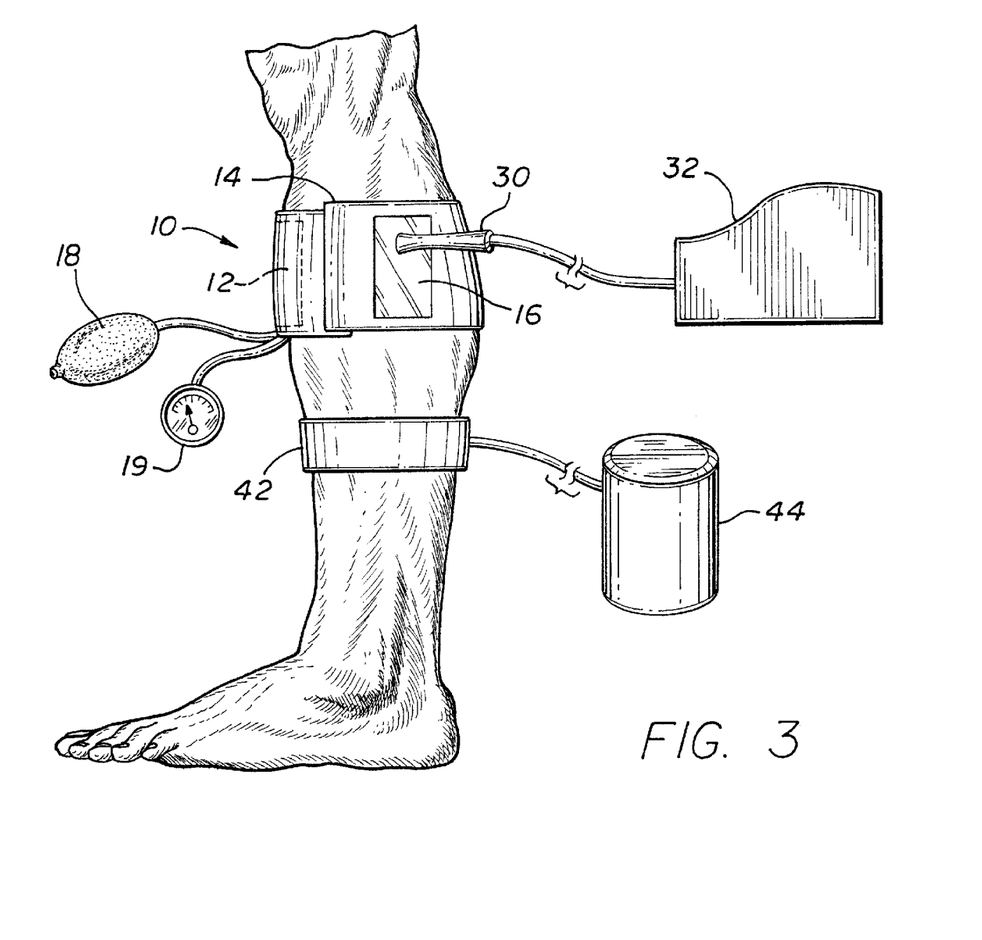
FIG. 3 is a perspective view of the pressure tourniquet wrapped around a limb of a patient, and an ultrasound transducer located at the window in accordance with aspects of the present invention.

Referring also to FIG. 3, the window 16 is substantially transparent to ultrasound to allow an ultrasound transducer 30 to engage the window and ascertain the condition of the vein in the limb to be treated. Parameters such as the vein diameter and the flow of blood through the vein may be ascertained in assessing the condition of the vein. The ultrasound transducer is preferably connected to an ultrasound imaging system 32 for determining the condition of the vein. For ultrasonic imaging, air is not an effective medium, so the transducer is put into direct contact with the window 16. An acoustic transmission gel is placed on and under the ultrasound window to facilitate ultrasound transmission from the transducer through the window to the skin. The gel prevents air gaps from forming between the skin and the window and between the ultrasound transducer and the window. The use of ultrasound can provide information regarding the location of incompetent valves, the patency of a vein, including the diameter of the vein, and the existence of reflux in the vein. Such ultrasound techniques are well known, and are discussed in greater detail in U.S. Pat. No. 5,730,136 entitled "Venous Pump Efficiency Test System and Method" which is hereby incorporated by reference.

FIG. 3 illustrates the tourniquet 10 wrapped around a patient's limb, in this case a leg, but may also be applied to other anatomical structures. The tourniquet is secured to the limb by the fastener 14. Where the fastener is a hook and loop system, the hook portion of the fastener can engage the loop portion behind the bladder 12 on the tourniquet. The window 16 remains unobstructed and is directly in contact with the limb. The tourniquet 10 placed around the leg can apply external compression to alter the vein diameter and allow ultrasound detection of reflux and the diameter of the vein under the window.

A dilated vein in the limb can be viewed using an ultrasound transducer 30 placed against and in contact with the window. The ultrasound transducer is preferably capable of duplex scanning and can provide signals to an ultrasound imaging apparatus 32 for evaluating and detecting dilation of the vein and separation of the vein valves and reflux which is an indication of valvular incompetency. Locating sites of valvular incompetency can be achieved by taking such measurements through the ultrasound window. Duplex ultrasound can be used to locate vein valves by imaging the vein to observe a bulging of the vein which would be the valve sinus proximal to the annulus where the valves are attached to the vein wall. Under certain conditions, the valve leaflets themselves may be observable through ultrasound imaging. The turbulence of flow can be determined using color flow signals mapped onto the vein in order to locate the valves. Ultrasound can also be used to identify the more echogenic tissue at the valve annulus. Ultrasound can also be used to locate a valve just distal to a branch vein or perforating vein connected to the vein under examination. However, in patients with incompetent vein valves in varicose veins that are significantly over dilated, some of the aforementioned techniques for valve identification are less useful. For example, the valve sinus may be difficult to locate in such varicose veins.

The pressure tourniquet can be placed on a limb, with the ultrasound window placed over suspected valve sites. The tourniquet is inflated to reduce the vein diameter and obtain valve closure, thereby reducing or abolishing reflux. This method can be used to confirm that a structurally intact vein valve is present under the tourniquet. To further localize the axial location of a valve, a narrow width pressure tourniquet, such as between two and three inches (between 5 and 8 cm), having an ultrasound window can be used to isolate and locate specific valves in the vein. Patients with a history of phlebitis or thrombosis in the vein may have structurally damaged or atrophied vein valves. The pressure tourniquet with the ultrasound window will be capable of reducing these vein diameters. However, if reflux is not significantly reduced, an irreparable valve may have been identified.

A localized assessment of reflux and the effects of external compression can be determined under duplex guidance by ultrasound imaging through the tourniquet. Information for the selection and screening of patients for venous procedures can be obtained in a non-invasive manner. The tourniquet alters the vein diameter and duplex ultrasound scanning is used to identify valves in both the deep and the superficial venous systems and to identify patients in which decreasing the vein diameter would reduce reflux. An indication of the existence of a structurally intact venous valve is the significant reduction or abolition of reflux when the vein diameter is reduced. Altering the vein diameter an appropriate amount by external compression with the tourniquet, an expandable electrode catheter can be introduced into the vein to mold the vein to the appropriate diameter to reduce reflux.

Figure 4:
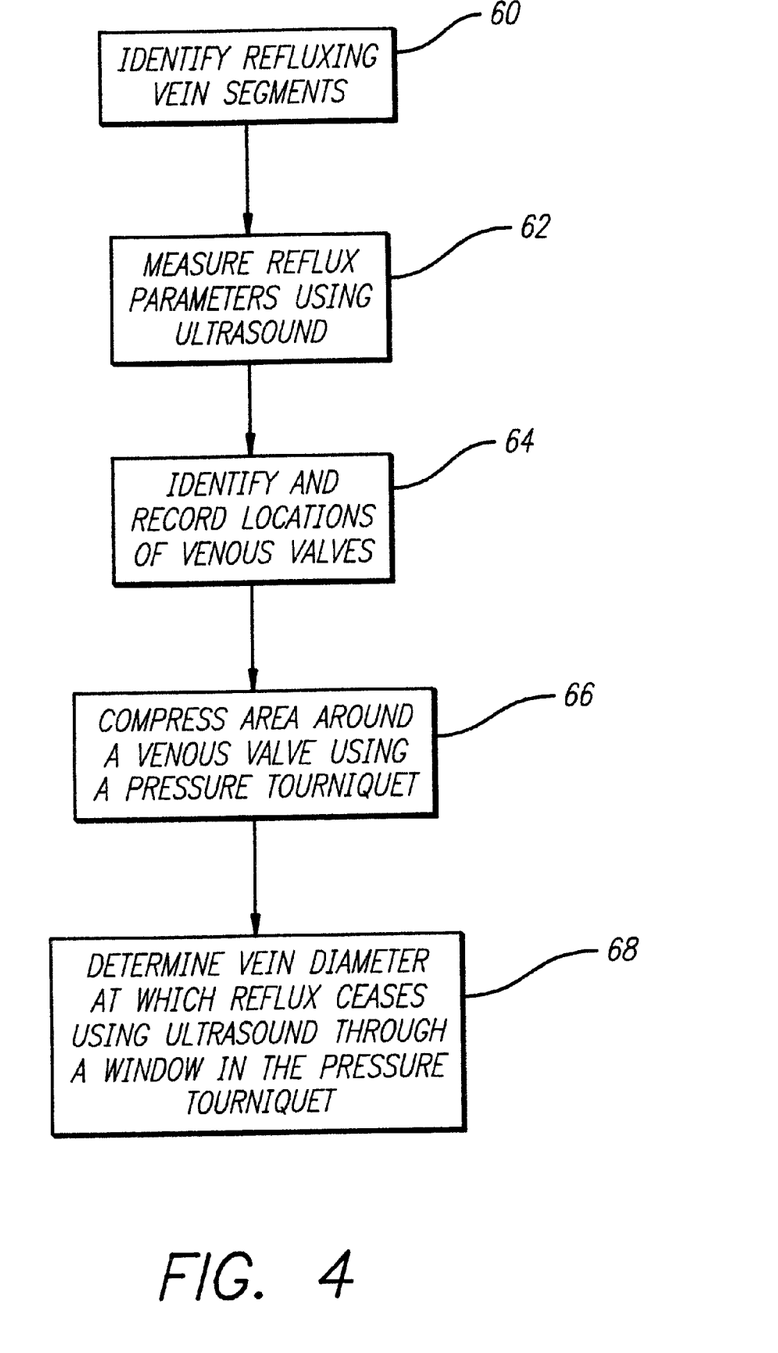
FIG. 4 is a flow chart outlining a diagnostic procedure using the tourniquet of FIG. 1 in accordance with aspects of the present invention.

The tourniquet can be used in conjunction with ultrasound to evaluate whether reducing the diameter of a vein would significantly reduce reflux in a patient with venous insufficiency. This evaluation procedure is outlined in the flow chart shown in FIG. 4. Vein segments exhibiting reflux are identified 60, preferably by using duplex ultrasound. Any observable valve sites of the patient are also identified and marked. The magnitude of reflux with the patient standing is also measured using ultrasound 62, including the parameters of average velocity of reflux, peak velocity of reflux, duration of reflux, and the total volume of reflux. These measured parameters are preferably taken over a period of two seconds. The location of incompetent venous valves are identified and recorded 64. The pressure tourniquet is wrapped around the limb containing the refluxing veins 66. The echo-lucent window of the pressure tourniquet is placed over the valve site of a vein exhibiting reflux. Where the refluxing vein is a superficial valve, the tourniquet should be placed with minimal wrapping pressure to avoid compressing the superficial vein. The diameter of the vein covered by the tourniquet should be measured by ultrasound. The pressure of the tourniquet is adjusted to compress the limb and reduce the vein diameter to the amount required to reduce reflux 68. The pressure of the tourniquet is preferably adjusted to reduce the diameter of the vein in intervals so that the vein diameter is reduced by, for example, 20%, 33%, and 50%. The vein can be reduced beyond 50% if necessary to reduce or eliminate reflux. However, if the vein diameter must be reduced to the point at which the vein is effectively ligated in an attempt to reduce or eliminate reflux, this is an indication that the vein valve is irreparable. A second tourniquet or manual limb compression can be used approximately five centimeters distal to the first tourniquet to provide distal compression. While distal compression and release is being applied to the patient, the parameters of venous reflux can be measured by ultrasound through the window of the first tourniquet to determine the effective diameter at which reflux is reduced or eliminated.

Venous blood flow can be augmented by compression techniques to control blood flow through the vein and venous valves under treatment to further confirm the diagnosis. The bladder 12 of the tourniquet 10 can be inflated further to compress the tissue of the limb surrounding the vein in order to force blood through the vein. Some blood may be forced out of the area undergoing treatment and to the next venous valvular level. The area under compression may include several incompetent venous valves. The bladder is then deflated to the point where the compressive pressure intially appeared to restore valvular competency for venous function. Reflux in the previously compressed vein can then be detected using the ultrasound transducer in contact with the window to determine whether the valves have properly closed.

A separate second tourniquet 42, as illustrated in FIG. 3, can be placed distal to the tourniquet 10 in order to perform distal compression. The separate tourniquet 42 can be controlled by a pneumatic source 44. The use of a separate tourniquet allows distal compression of the venous system. Compressing the limb distal to the tourniquet 10 can augment antegrade flow. Rapid release of this compressive force while the patient is upright, or tilted with the feet down, can be used in determining reflux in the venous system.

Figure 5:
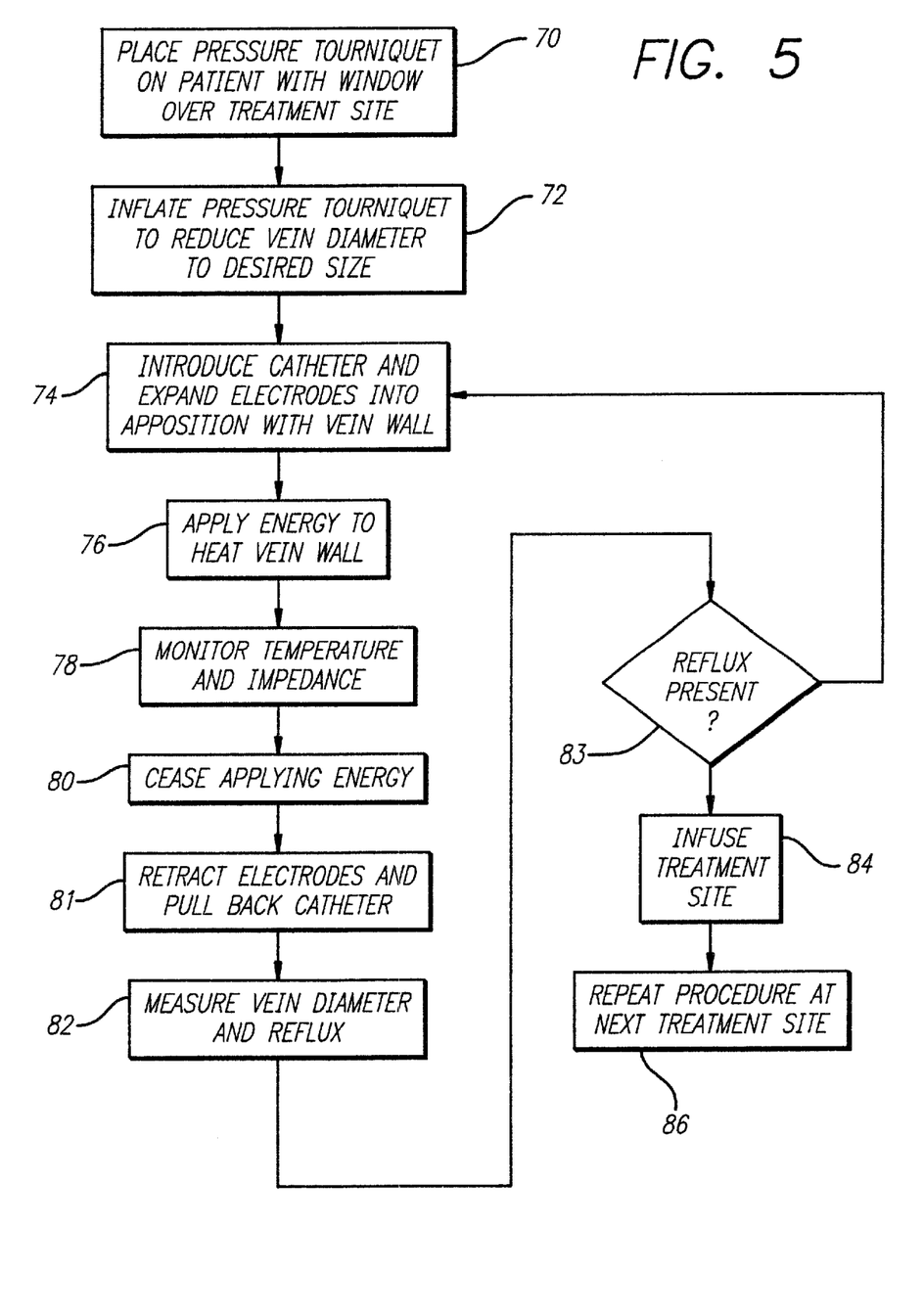
FIG. 5 is flow chart outlining a procedure of treating veins using the tourniquet and electrode catheter in accordance with aspects of the present invention.

An expandable electrode catheter is used in conjunction with the pressure tourniquet to mold the- vein to a reduced diameter to reduce or eliminate reflux. This treatment procedure is outlined in the flow chart of FIG. 5. Heparin can be infused through the vein before the vein diameter is reduced in order to prevent thermally-induced coagulation. The pressure tourniquet is placed on the patient with the ultrasound window over the vein treatment site 70. The pressure tourniquet is inflated 72 to reduce the vein diameter to a desired size to reduce or eliminate reflux. A 20% to 50% reduction in the vein diameter is often sufficient to restore valvular competency and reduce reflux, although a greater reduction may be necessary. From an antegrade approach, the catheter is introduced such that the electrodes are distal to the valve annulus. The electrodes are expanded to come into apposition with the vein wall 74. The electrodes apply energy 76, such as RF energy, to heat the tissue of the vein wall. The temperature and impedance of the treatment site is monitored 78. Overheating and coagulation are to be avoided. Energy is delivered for a predetermined time, such as for forty-five seconds after the temperature level of the treatment site is stabilized 80. It has been found that by heating the vein by applying RF energy for a period of between thirty seconds and two minutes is often sufficient to mold the vein to durably assume a reduced diameter. After the application energy is ceased 80, the electrodes are retracted and the catheter is pulled back 81 from the treatment site. Vein diameter and the existence of reflux are reassessed 82 by ultrasound through the window with the electrodes retracted and the tourniquet deflated. The energy applying step 76 or the vein sizing step 72 can be repeated if reflux is detected 83, otherwise, the treatment area can be infused 84 with heparin or another medicant. Other venous sites can then be treated 86.

Figure 6:
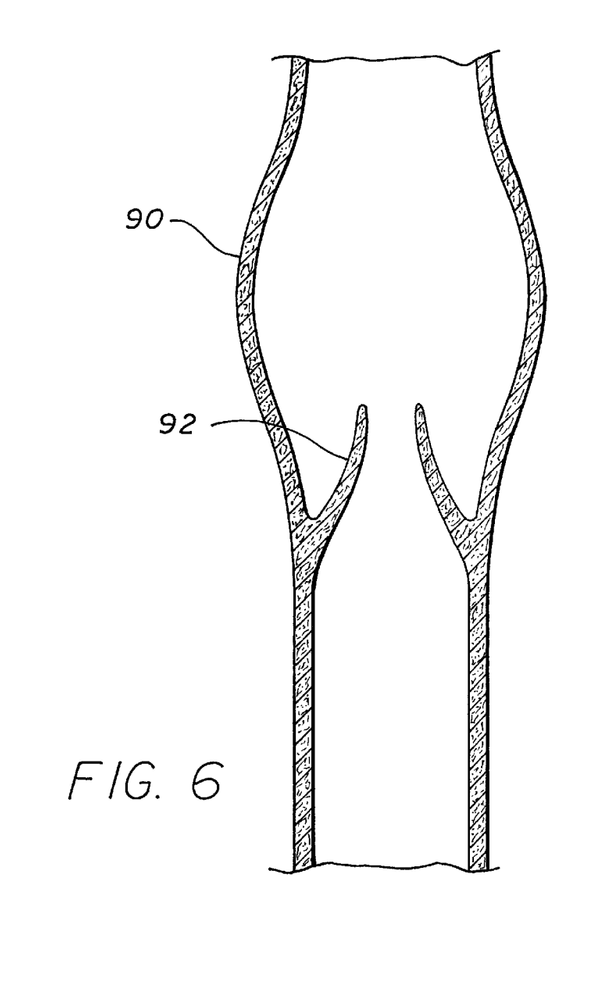
FIG. 6 is a side view of a dilated vein with an incompetent valve.

FIG. 6 illustrates a dilated vein 90 with an incompetent valve 92 in the limb before pressure is applied by inflating the bladder of the tourniquet. As the bladder is inflated, the tourniquet clamps down onto the limb to compress the limb, as generally illustrated by the arrows on either side of the vein in FIGS. 7 and 8. By externally compressing the limb with the pressure tourniquet, the diameter of the dilated vein 90 is reduced by the surrounding tissue of the limb. A suitable fluid such as air is introduced into the bladder of the tourniquet by the hand pump 18 to inflate the bladder and compress the limb until the diameter of the vein is adequately reduced to the point where venous function and valvular competency are restored. This condition can be recognized when reflux is no longer detected in the vein by ultrasound through the window 16. Thus, the proper diameter for restoring venous function can be determined while diagnosing venous reflux and valvular incompetency.

Figure 7:
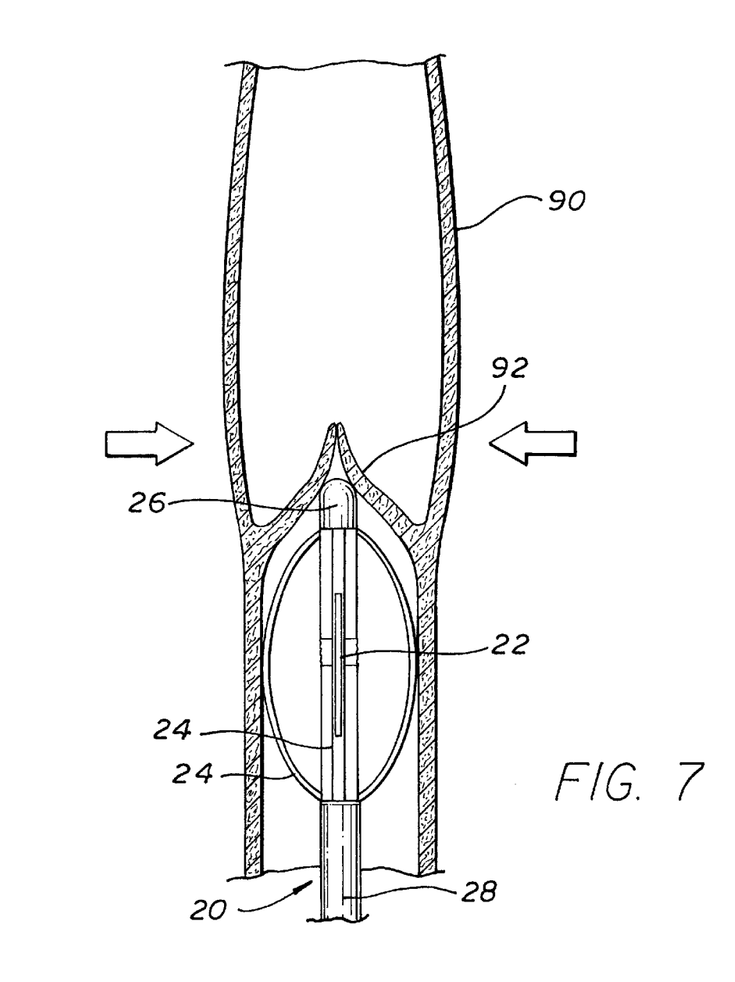
FIG. 7 is a side view of the vein of FIG. 6 which has been compressed to a reduced diameter by the external pressure tourniquet, and an electrode catheter having electrodes expanded into apposition with the vein wall, in accordance with the present invention.

As illustrated in FIG. 7, the catheter 20 delivers electrodes 22 to a venous treatment site. As indicated by the arrows, external pressure by the tourniquet 10 has reduced the vein diameter to the diameter at which reflux is abolished. The electrodes 22 at the working end of the catheter 20 are brought into apposition with the vein wall in order to cause localized heating of the surrounding venous tissue, cause collagen contraction, and molding of the vein in order to restore the competency of a venous valve and the function of the vein. A description of suitable electrode catheters and methods of use can be found in U.S. Application Ser. No. 08/610,911, which is hereby incorporated by reference. Although the catheter is shown in the figures as approaching the venous treatment site in an antegrade manner, it is to be understood that the catheter can approach the treatment site in a retrograde manner as well.

Figure 8:
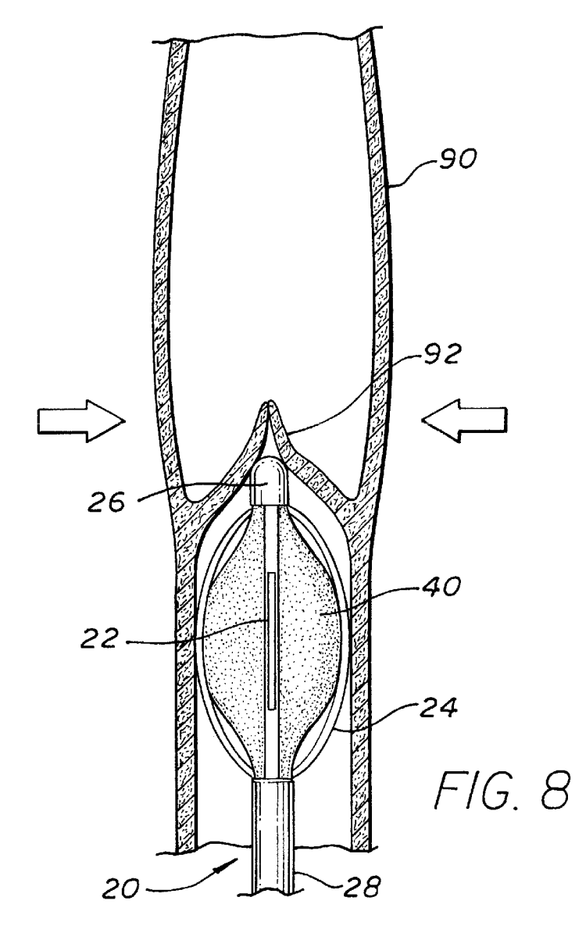
FIG. 8 is a side view of the vein of FIG. 6 which has been compressed to a reduced diameter by the external pressure tourniquet, where another embodiment of the electrode catheter is introduced antegrade into the vein with electrodes expanded into apposition with the vein wall.

The catheter can be introduced over a guide wire (not shown) through the venous system. The electrodes 22 are then placed in apposition with the vein wall, preferably by bowing the electrodes away from the catheter 20, as illustrated in FIGS. 7 and 8. The catheter in FIG. 8 is an alternate embodiment having a balloon to occlude the vein during treatment to limit the influence of blood flow during treatment. While the electrodes 22 are apposed with the vein wall, compressive pressure, as generally illustrated by the arrows in FIGS. 7 and 8, is still being applied by the tourniquet. RF energy is applied by the electrodes of the catheter in order to heat the vein wall, cause collagen contraction, and mold the vein diameter to the reduced diameter produced by the compressive force of the external tourniquet. The application of RF energy to the vein wall by the energized electrodes causes the vein to become heated and durably assume the reduced diameter. An RF generator (not shown) is activated to provide suitable RF energy to the electrodes, preferably at a low power level, and preferably at a selected frequency from a range of 250 kHz to 350 MHZ. For example, suitable frequencies include 450 kHz and 510 kHz. One criterion for the selection of the applied frequency is to manage electrical losses in the leads supplying power to the electrodes. Another criterion is compatibility with filter circuits which can be used to eliminate RF noise from thermocouple signals.

The properties of the treatment site, such as temperature, may be monitored to provide feedback control for the RF energy. Monitoring such values in an automatic feedback control system for the RF energy may also be used to control the heating effect and avoid overheating of the vein.

The energy emitted from the electrodes is converted within the venous tissue into heat. As the temperature of the venous tissue increases, the venous tissue can begin to durably assume the reduced diameter, due in part to the structural transfiguration of the collagen fibers in the vein. Although the collagen becomes compacted during this process, the vessel with collagen still retains elasticity. The vein would shrink further but for the mechanically bowed out electrodes defining the effective diameter of the catheter. Other schemes, such as a balloon or a helical member which can be coiled and uncoiled, may be used to mechanically limit or control the amount of shrinkage in the vein or to displace blood from the treatment site. Such mechanical schemes assure apposition between the electrodes and the venous tissue during treatment, and prevent further shrinkage so that the vein remains patent.

Figure 9:
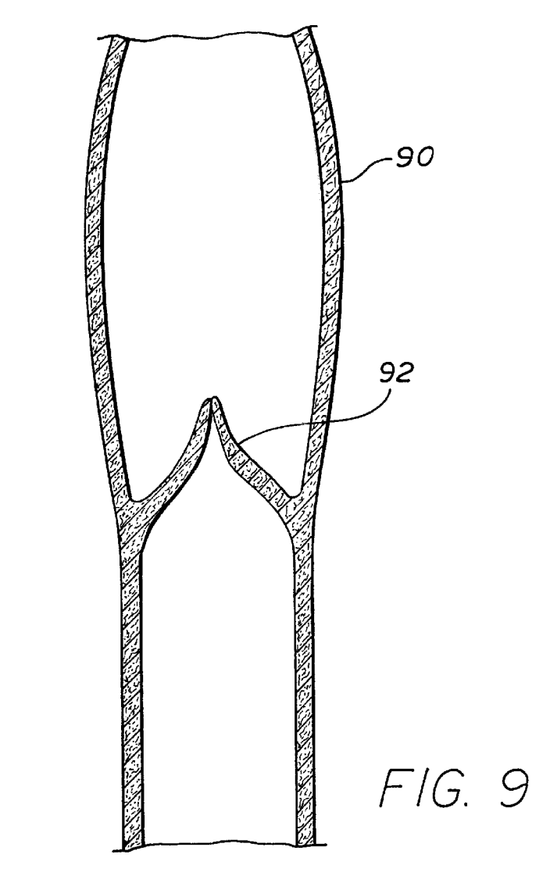
FIG. 9 is a side view of the vein of FIG. 6 after treatment by the electrode catheter and removal of the pressure tourniquet from the limb in accordance with the present invention.

The effective diameter of the catheter is not mechanically adjusted during the treatment with RF energy. The vein is already compressed by the tourniquet to a reduced diameter. By heating the wall of the compressed vein, the vein is effectively molded to equal the reduced diameter caused by the external pressure tourniquet, so that when the compressive force of the pressure tourniquet is released, as illustrated in FIG. 9, the vein remains in its reduced diameter condition. The heating effect can also cause some thickening of the vein wall as part to the structural transfiguration of the collagen fibers in the vein.

Vein diameter reduction is achieved in a controlled manner which does not require the operator to adjust the electrode diameters during heating. The electrodes of the catheter need not be expanded to the enlarged diameter of a dilated vein, and smaller diameter catheters may be used in conjunction with the tourniquet. The use of ultrasound avoids the need for the contrast medium required for the x-ray imaging of a vein. Ultrasound typically does not have the image resolution that would allow an operator to precisely determine the effective diameter defined by the electrodes being adjusted to maintain contact with the vein. The use of a tourniquet having an ultrasound window allows precise control over the vein diameter reduction to eliminate or reduce reflux without having to perform fine mechanical adjustments to the diameter defined by the bowable members and the electrodes of an expandable catheter during treatment. The tourniquet sets the final desired diameter of the vein by externally compressing the anatomical structure surrounding the vein and monitoring the vein size reduction by ultrasound until that desired diameter has been reached. In addition to the vein diameter, the presence and elimination of reflux can be monitored by ultrasound. After the desired diameter for the vein is achieved, the expandable catheter is advanced to the vein site and the electrodes expanded away from the catheter until contact with the vein wall is determined. Such contact can be ascertained by measuring impedance. Physical contact may also be felt by the operator through the expansion control apparatus at the proximal end of the catheter. Energy is then applied to mold the vein to the reduced diameter caused by the compressive force of the pressure tourniquet. The use of a tourniquet having an ultrasound window allows precise control over vein diameter reduction without having to perform fine mechanical adjustments to the diameter defined by the bowable members and the electrodes during treatment.

One embodiment of the catheter 20 having electrodes 22 for causing localized heating of the surrounding venous tissue and shrinkage of the vein includes conductive elongate members 24 which can be bowed outward, as illustrated in FIG. 7. The extent of shrinkage is controlled by the effective diameter of the catheter and the electrode combination. The electrodes 22 are bowed radially outward as part of the effective diameter of the catheter so as to come into apposition with the vein wall. RF energy is applied from the electrodes, which are preferably bipolar electrodes, and the vein becomes heated. The vein becomes fixed in its reduced diameter configuration caused by the compression of the tourniquet, as a result of this heating effect. The vein would shrink further but for the bowed elongate members 24. The final diameter of the vein is the final effective diameter of the catheter, as defined by the electrodes and the bowed members.

The catheter 20 includes a tip 26 which is attached to one end of each elongate member, and the other end of each member is connected to a sliding outer sleeve 28 formed along the exterior of the catheter shaft. The outer sleeve 28 extends down the length of the catheter to allow the physician to directly and mechanically control the effective electrode diameter during the application of RF energy. As the slidable sleeve 28 is moved towards and away from the working end, the electrodes 22 are urged radially outwardly and inwardly, respectively. The tip 26 essentially remains stationary while the slidable sleeve is moved. Moving the sleeve 28 back toward the connecting end of the catheter places the members against the catheter before insertion into or withdrawal from the vein. Moving the sleeve 28 forward toward the working end of the catheter causes the members to deflect and radially bow outward to an increased diameter. The contact area of the electrodes is bowed outwardly as the opposite ends of the elongate members are moved closer together, which places the electrodes in apposition with the venous tissue to be treated. By manipulating the slidable sleeve to adjust the effective diameter defined by the radial bowing of the elongate members, contact between the electrodes and the vein wall can be maintained.

A switch, lever, threaded control knob, or any other suitable mechanism, can be used by the operator to provide fine control over the movement of the slidable sleeve. The effective diameter of the electrode can be controlled for treating vein lumen having different diameters, and for preventing shrinkage of the vein beyond the reduced diameter created by the pressure tourniquet to restore venous function or valvular competency.

The bowable elongate members 24 can be fabricated from stainless steel, spring steel, or Nitinol®, and would preferably be biased to return to a reduced diameter profile. The members are preferably sized to allow four, six, eight, or more members carrying electrodes around the catheter shaft.

The bowable member 24 can be conductive in order to act as an electrode, and insulation is provided over the majority of the conductive surface in order to prevent RF heating of areas other than the vein wall contacted by the electrodes. Only a modest portion of the conductive surface is exposed to act as the electrode. The heating effect is greatest when the electrodes are close together because the electrical field density or power density is greatest at this point. The ends of the members are insulated from each other to prevent creating electrical field densities that are larger at the ends compared to that around the middle of the electrode. As the effective diameter increases, greater field disparities between the ends and the outwardly bowed midsections could be created if no insulation were provided. The insulation can be polyimide, parylene, or another type of insulating material. The insulation provided along the sides and the back of the electrodes opposite from the vein wall further prevents heating of the blood flowing in the vein, and reduces the likelihood of coagulation. Where the member 24 has a rectangular shape, then the exposed area which functionally acts as the electrode would then occupy only one face of that member.

The electrode 22 is preferably in direct contact with the vein wall 90 during apposition to focus the heating effect into the vein wall. The exposed surface area of the electrode should be as great as allowable while maintaining a consistent distance between the exposed sections of the members along the circumference of the effective diameter. The polarity of each electrode is preferably opposite to the polarity of the immediately adjacent electrodes to provide for omnidirectional energy application and circumferential shrinkage of the vein. Thus, a relatively uniform RF field would be created along the circumference of the catheter by the alternating electrodes. If the RF field was not substantially uniform, shrinkage of the vein may be concentrated where the RF field was strongest. The electrodes could be arranged so that a localized directional heating effect could be produced if desired.

It is to be understood that although a bipolar arrangement is described, a monopolar arrangement may also be used. In a monopolar arrangement, an inside. electrode, such as a metalized balloon, mesh, or bowable wire electrode, is inserted into a patient's body. An outer electrode having a much larger surface area than the inside electrode is placed on the outer surface of the patient's body near the treatment site. For example, an external metal mesh may formed as part of the tourniquet in order to be placed on the skin as an inactive larger electrode over the region to be treated by the inside electrode. The electrodes are connected to an RF generator which produces an electric field within the patient's body. Because the surface area of the inner electrode is much smaller than that of the outer electrode, the density of the electric field is much higher around the inside electrodes. The electric field reaches its highest density between the two electrodes in the region near the inside electrode. The increased density of the field around the inside electrode allows localized heating of the tissues surrounding the inside electrode. The degree of heating may be dependent on such factors as the impedance and dielectric constant of the tissue being heated.

The catheter can further include a guide wire lumen (not shown) for accepting a guide wire. The guide wire lumen is preferably insulated so as to prevent or minimize any coupling effect the electrodes may have on the guide wire. The guide wire lumen can also allow for the delivery or perfusion of x-ray contrast agents, anticoagulants, other medicants, or a cooling solution to the treatment area during application of the RF energy. The delivered cooling fluid minimizes any heating effect on the blood so as to avoid of heating the blood to the point of coagulation.

A sensor such as a thermocouple for measuring temperature (not shown) can be attached to the electrode 22. The temperature sensor can be soldered in place through a hole in the electrode so that the sensor is substantially flush with the exposed surface of the electrode. The sensor can accurately sense the temperature of the vein wall in apposition with the exposed electrode surface.

As illustrated in FIG. 8, a balloon 40 can be located between the catheter shaft and the elongate members 24. The balloon 40 may be fabricated from either an elastic material, such as silicone rubber or latex, or a noncompliant material. The balloon 40 is inflated and comes into contact with the elongate members 24. The balloon can be inflated either before or after the electrodes are placed in apposition with the vein wall. Where the balloon is inflated before the electrodes are apposed, the balloon physically moves the bowable members and electrodes into apposition with the vein wall. As the balloon 40 is further inflated, the electrodes 22 are moved outwardly in a radial direction as the elongate members are deflected and bowed by the expanding balloon 40. Where the balloon is inflated after the electrodes are apposed with the vein wall, the balloon is merely inflated to the effective diameter defined by the electrodes. When the proper diameter is reached, the inflation of the balloon ceases, and the application of the RF energy begins.

The balloon 40, in addition to controlling the amount of venous shrinkage, occludes the blood flow in the vein in order to provide more consistent and predictable shrinkage of the vein by reducing the effect of blood flow carrying heat away from the treatment site. As RF energy is applied, the vein becomes heated and begins to permanently shrink down to the effective diameter of the catheter.

A second tourniquet 42 can be placed distal to the tourniquet 10 in the manner illustrated in FIG. 3, in order to prevent blood flow at the venous treatment site so that the heating effect for shrinking the vein is not affected by the blood flowing through the vessel. While the tourniquet 10 can be sized to cover a significant portion of the patient's leg or limb, the second tourniquet 42 is preferably more narrow. For example, if the tourniquet 10 covers a large portion of a patient's leg, then the second tourniquet 42 preferably narrower, having a width of between two and six inches (between 5 and 15 cm). As previously discussed, the second tourniquet can be used to provide distal compression, augment venous blood flow and diagnose the venous condition initially. The second tourniquet can also be used alone or in conjunction with the balloon in order to lessen the influence of blood flow in the vein carrying heat away from the treatment site.

RF energy is no longer applied from the electrodes after there has been sufficient heating of the vein so that the vein becomes molded to durably assume the reduced diameter caused by the external compressive force of the pressure tourniquet. The reduced diameter of the vein is the final effective diameter as defined by the diameter of the balloon 40 and the deflected elongate members 24. The balloon 40 is then is deflated to a minimal profile. The elongate members 24 in this embodiment can also be fabricated from stainless steel, spring steel, or nitinol biased to return to a reduced diameter profile when the balloon is deflated.

After treatment, the commissure and the cusps of the venous valve 92 should be closer together with little separation or prolapse, as illustrated in FIG. 9 which indicates a restoration of the competency of the valve 92. Valvular competence can be determined by ultrasound measurement for reflux through the window of the tourniquet 10. Reducing vein dilation in a section adjacent the segment containing the incompetent venous valve can many times restore valvular competency by reducing the necessary span of the cusps to achieve coaptation across the vein.

The catheter 20 and the tourniquet 10 can be repositioned so as to treat as many venous sections and valves as necessary. RF energy can be applied to each venous section to be repaired, until all of the desired venous sections are repaired and the valves are rendered competent. It is to be understood that other forms of energy including thermal energy and optical energy from a laser can be used to mold the vein being treated. Multiple incompetent valves and dilated venous sections may be treated and repaired in a single minimally invasive procedure.

Figure 10:
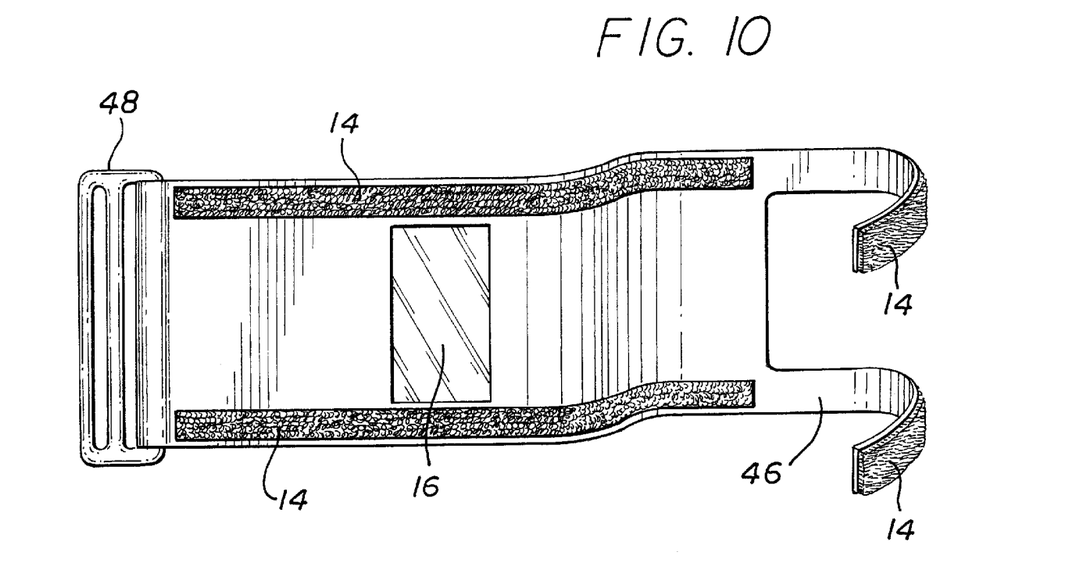
FIG. 10 is a side view of another embodiment of the pressure tourniquet in accordance with aspects of the present invention.

Another embodiment of the tourniquet 10 is illustrated in FIG. 10, which uses straps 46 to achieve the desired compressive pressure on the limb. The straps are configured to not obstruct the window 16 so that ultrasound measurements can be taken for the vein to be treated. The straps may use a fastener 14 such as a hook and loop system, snaps, or other suitable means which can form a tourniquet around the limb. A fixed loop 48 constructed of metal, hard plastic, or other rigid materials, at one end of the tourniquet can be used to allow the straps 46 to be pulled back on the tourniquet to facilitate tightening and tensioning of the tourniquet snugly around a leg or other limb. The straps should be fed through and past the metal loop at one end of the tourniquet and pulled back and against the fastener so that the body of the tourniquet should surround the limb. Otherwise, the exposed area of the limb may not come under compressive pressure such that the vein is not properly compressed to a reduced diameter. The tourniquet can be adjusted to have any dimension which can allow compression of the anatomy surrounding the treatment site of the venous system. While a tourniquet having a narrow width may be used, a wider tourniquet would provide compression over a larger area to ensure that the venous section experiencing reflux or venous valvular incompetency is located and treated.

The ultrasound transducer is in contact with the window, and preferably can be moved relative to the window while maintaining contact with the window. In another embodiment of the tourniquet, an ultrasound transducer can be included as part of the tourniquet over the window which is transparent to ultrasound. The ultrasound transducer is connected to an ultrasound imaging apparatus for determining venous conditions underlying the window.

As can be readily ascertained from the disclosure herein, the procedure of the present invention is accomplished without the need for prolonged hospitalization or postoperative recovery. The curative restoration of venous function is possible without the need for continued lifestyle changes, such as frequent leg elevation, the wearing of relatively uncomfortable elastic support stockings or prolonged treatment of recurrent venous stasis ulcers. Moreover, the need for repair or surgical transplantation of veins would not be necessary.

Early treatment of venous disease could prevent more serious complications such as ulceration, thrombophlebitis and thromboembolism. The cost of treatment and complications due to venous disease would be significantly reduced. There would be no need for extensive hospitalization for this procedure, and the need for subsequent treatment and hospitalization would also be reduced from what is currently needed. Furthermore, the minimally invasive nature of the disclosed methods would allow the medical practitioner to repair or treat several venous sections in a single procedure in a relatively short period of time.

Although the invention has been described in relation to the treatment of the venous system of the lower limbs, it is to be understood that the invention is not limited thereto and may be employed intraluminally to treat veins in other areas of the body, as well as other lumen and hollow anatomical structures in the body. Furthermore, although the invention will be described as using RF energy from the electrode, it is to be understood that other forms of energy such as microwaves, ultrasound, direct current, circulating heated fluid, radiant light, and lasers can be used, and that the thermal energy generated from a resistive coil or curie point element may be used as well.

From the foregoing it will be appreciated that the system of the present invention provides advantages in diagnosing and treating venous insufficiency and venous incompetency.

While several particular forms of the invention have been illustrated and described, it will be apparent that various modifications can be made without departing from the spirit and scope of the invention.

What is claimed is:

1. An apparatus comprising:
    a tourniquet having a first section and a second section, wherein the second section has an inside surface and an outside surface;
    a compression device located on the first section of the tourniquet, and adapted to apply external pressure to a patient to compress the vessel to a reduced diameter; and
    a window substantially transparent to ultrasound and traversing the second section of the tourniquet from the inside surface to the outside surface, wherein the window is capable of allowing the vessel to be monitored by a separate ultrasound transducer placed on the window on the outside surface of the second section of the tourniquet when the tourniquet is applied to the patient.

2. The apparatus of claim 1, wherein the compression device comprises an inflatable bladder connected to a pneumatic inflation source.

3. The apparatus of claim 1, wherein the window has a thickness sufficient to prevent the window from being pulled away from the skin when the bladder is inflated.

4. The apparatus of claim 1, wherein the compression device comprises straps.

5. The apparatus of claim 1, further comprising a hook and loop fastening system for securing the tourniquet around a patient.

6. The apparatus of claim 1, wherein the window comprises a flexible polymer.

7. The apparatus of claim 1, wherein the window comprises nylon.

8. The apparatus of claim 1, wherein the window acts as a ultrasound stand-off.

9. The apparatus of claim 1, wherein the window comprises an enclosed gel pouch.

10. The apparatus of claim 1, wherein the window comprises a polyurethane film transparent to visible light.

11. An apparatus comprising:
    a tourniquet having a first end, a second end, a first area, and a second area, wherein the second area includes an inside surface and an outside surface;
    a pneumatic inflatable bladder located in the first area of the tourniquet;
    a fastener configured to connect the first end to the second end so as to hold the tourniquet around an anatomical structure, wherein the tourniquet compresses the anatomical structure when the bladder is inflated;
    a window substantially transparent to ultrasound, the window traversing the second area of the tourniquet from the inside surface to the outside surface, wherein the window is capable of allowing the vessel to be monitored by a separate ultrasound transducer placed on the window on the outside surface of the second section of the tourniquet when the tourniquet is applied to the patient.

12. The apparatus of claim 11, wherein the window comprises a flexible material.

13. The apparatus of claim 11, wherein the window comprises nylon.

14. The apparatus of claim 11, wherein the window acts as a standoff.

15. The apparatus of claim 14, wherein the window comprises an enclosed gel pouch.

16. The apparatus of claim 11, wherein the window comprises a polyurethane film transparent to ultrasound and visible light.

17. The apparatus of claim 11, wherein the first area is separate from the second area of the tourniquet, the fastener is located at the first end, and the second area is located between the first area and the fastener.

18. The apparatus of claim 11, wherein the tourniquet is configured so that the window overlies the anatomical structure when the tourniquet is held around the anatomical structure by the fastener, and the window allows a view of the anatomical structure by ultrasound.

19. A kit for controllably shrinking a selected vein of a patient, comprising:
   a compression device adapted to apply external pressure to the patient over a selected vein position to compress the vein to a reduced diameter;
   an expandable catheter adapted for insertion into the vein of the patient, the catheter having an expandable device capable of contacting the reduced diameter of the vein and imparting energy to the vein to reduce the diameter of the vein, the expandable device having sufficient structural strength to prevent the diameter of the vein from being reduced further while energy is being imparted to the vein; and
   the compression device including a window substantially transparent to a selected energy and located so that it is overlying the reduced diameter portion of the vein wherein the reduced diameter portion of the vein and the catheter can be viewed by the selected energy through the window.

20. The kit of claim 19 wherein the window is formed of a material that is transparent to ultrasonic energy.

21. The kit of claim 19 wherein the window comprises nylon.

22. The kit of claim 19 wherein the window comprises a flexible polymer.

23. The kit of claim 19 wherein the window acts as an ultrasound stand-off.

24. The kit of claim 23 wherein the window comprises a gel pouch.

25. The kit of claim 19 wherein the window comprises a polyurethane material transparent to ultrasound and visible light.

26. The kit of claim 19 wherein the compression device comprises an inflatable bladder.

27. The kit of claim 19 wherein the compression device includes a hook and loop fastening system for securing the tourniquet around a patient.

28. An apparatus comprising:
   a tourniquet having a first section and a second section, wherein the second section has an inside surface and an outside surface;
   means for applying external pressure to a patient over a vessel to compress the vessel to a reduced diameter, wherein the means for applying external pressure is located on the first section of the tourniquet;
   means for allowing ultrasound monitoring of the vessel, wherein the means for allowing ultrasound monitoring of the vessel traverses the second section of the tourniquet from the inside surface to the outside surface, such that the apparatus allows a separate ultrasound transducer to be placed on the means for allowing ultrasound monitoring of the vessel at the outside surface of the second section of the tourniquet when the tourniquet is applied to the patient.

29. The apparatus of claim 22, wherein the means for applying external pressure includes an inflatable bladder connected to a pneumatic inflation source.

30. The apparatus of claim 22, wherein the means for allowing ultrasound monitoring of the vessel has a thickness sufficient to prevent the means for allowing ultrasound monitoring of the vessel from being pulled away from the skin when the bladder is inflated.

31. The apparatus of claim 22, wherein the means for applying external pressure includes straps.

32. The apparatus of claim 22, further comprising a hook and loop fastening system for securing the tourniquet around a patient.

33. The apparatus of claim 22, wherein the means for allowing ultrasound monitoring of the vessel comprises a flexible polymer.

34. The apparatus of claim 22, wherein the means for allowing ultrasound monitoring of the vessel comprises nylon.

35. The apparatus of claim 28, wherein the means for allowing ultrasound monitoring of the vessel acts as a ultrasound stand-off.

36. The apparatus of claim 28, wherein the means for allowing ultrasound monitoring of the vessel comprises a gel pouch.

37. The apparatus of claim 28, wherein the means for allowing ultrasound monitoring of the vessel comprises a polyurethane film transparent to visible light.

* * * * *

UNITED STATES PATENT AND TRADEMARK OFFICE
CERTIFICATE OF CORRECTION

PATENT NO.    : 6,361,496 B1
DATED         : March 26, 2002
INVENTOR(S)   : Arthur W. Zikorus et al.

It is certified that error appears in the above-identified patent and that said Letters Patent is hereby corrected as shown below:

Title page,
Item [62], Related U.S. Application Data, change "Jun. 2, 1997", to read -- Jun. 27, 1997 --.
Item [56], FOREIGN PATENT DOCUMENTS, change "WO 95/10322  4/1920" to -- WO 95/10322  4/1995 --.

Column 1
Line 6, change "Jun. 2, 1997" to -- Jun. 27 1997 --.

Column 16,
Lines 20, 23, 28, 30, 33 & 36, change "22", to -- 28 --.

Signed and Sealed this

Eighth Day of October, 2002

*Attest:*

JAMES E. ROGAN
*Director of the United States Patent and Trademark Office*

*Attesting Officer*